United States Patent
Helgason

(10) Patent No.: US 7,052,721 B2
(45) Date of Patent: May 30, 2006

(54) RECOVERY OF COMPOUNDS USING A NATURAL ADSORBENT

(76) Inventor: Hafsteinn Helgason, Barmahlid 39, IS-105 Reykjavik (IS)

( * ) Notice: Subject to any disclaimer, the term of this patent is extended or adjusted under 35 U.S.C. 154(b) by 525 days.

(21) Appl. No.: 10/240,650

(22) PCT Filed: Apr. 5, 2001

(86) PCT No.: PCT/IS01/00009

§ 371 (c)(1),
(2), (4) Date: Oct. 4, 2002

(87) PCT Pub. No.: WO01/77230

PCT Pub. Date: Oct. 18, 2001

(65) Prior Publication Data

US 2003/0118715 A1     Jun. 26, 2003

(30) Foreign Application Priority Data

Apr. 5, 2000     (IS) ......................................... 5429

(51) Int. Cl.
*A61K 35/60* (2006.01)
(52) U.S. Cl. .................... 424/543; 514/2; 514/21
(58) Field of Classification Search .............. 424/543; 514/2, 21
See application file for complete search history.

(56) References Cited

U.S. PATENT DOCUMENTS 3,906,112 A   9/1975 Anderson
4,505,936 A   3/1985 Meyers et al.
5,210,186 A   5/1993 Mikalsen

FOREIGN PATENT DOCUMENTS

| CA | 1313835  | 2/1993  |
| DK | 100686   | 12/1964 |
| EP | 077583   | 4/1983  |
| JP | 03290480 | * 1/1990 |
| JP | 7118226  | 5/1995  |
| JP | 9301950  | 11/1997 |
| JP | 11049972 | 2/1999  |
| NO | 147365   | 12/1982 |
| WO | 90/05767 | 5/1990  |

OTHER PUBLICATIONS

Database STN International, Document NO. 100:73435, Yang, Tony C. et al.: "Absorption of Metals by natural polymers generated from sefood processing wastes". XP00290124, abstract & ind, *Eng. Chem.Prod.res.Dev.*, 23(1):168-172 (1984).
Patent abstract of Japan 10(139) (C-348), May 22, 1986 & JP 60 262589 (Shiyuuzou Nakazono), Dec. 26, 1985.
JP 60 262859 (A), 10(139) (C-348), May 22, 1986, Dec. 26, 1985.

* cited by examiner

*Primary Examiner*—Jean C. Witz
(74) *Attorney, Agent, or Firm*—Hunton & Williams

(57) ABSTRACT

The invention provides a method for recovery of compounds by adsorption fish scales. The method can be used for natural and synthetic compounds such as various natural pigments including astaxanthin in an esterified or not and synthetic astaxanthin in free form, or other carotenoid compounds. Fish scales with an adsorbed compound may be used as a source of the compound both for human and animal consumption. In particular, fish scales with adsorbed astaxanthin provide a calcium-rich nutritional supplement with beneficial anti-oxidant properties.

33 Claims, 2 Drawing Sheets

110 x        760 x        2500 x 110 x        760 x        2500 x

RECOVERY OF COMPOUNDS USING A NATURAL ADSORBENT

FIELD OF THE INVENTION

Figure 1:
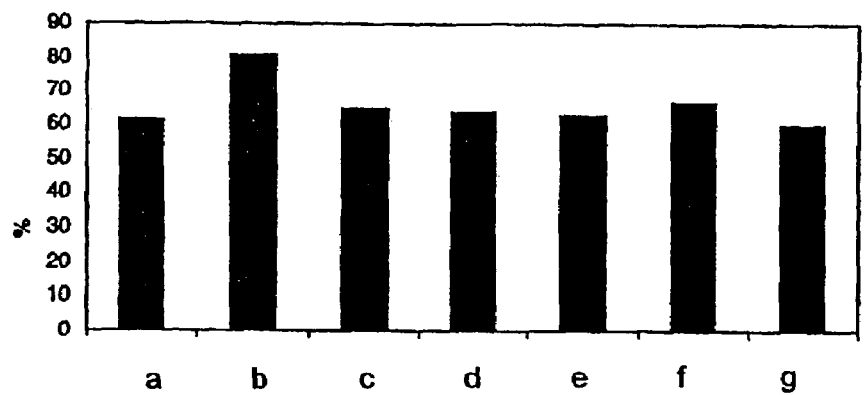

The present invention is within the field of purification, production and utilization of organic compounds such as natural and synthetic pigments. Specifically, a natural adsorbent substrate comprising fish scales is provided and a method for adsorbing compounds from solution media.

TECHNICAL BACKGROUND AND PRIOR ART

Coloring agents are commonly used as additives in the manufacturing of food products, pharmaceuticals and hygienic products. Commercial coloring agents can be synthetic substances which are normally referred to as dyes or azodyes, or the agents can be pigments of natural origin, e.g. in the form of plant material containing the pigment or as more or less purified pigments extracted from plants, animals or microorganisms. Occasionally, food grade or pharmaceutically acceptable coloring agents are provided in the form of synthetic or artificial substances having the same chemical composition as naturally occurring pigments. These types of coloring agents are also referred to in the art as natural identical colors. However, in the present context the terms "natural compound" and "natural pigment" are used exclusively to designate compounds and pigments which are derived from natural sources.

Many natural organic pigments have some common chemical properties, relating to the conjugated systems of carbon-carbon double bonds with or without heteroatoms, that provide the conjugated pi electron systems with low energy excitation states that absorb visible light and render those compounds their color.

Other types of compounds that may be found and isolated from natural sources include natural flavorings, nutrients and pharmaceutical compounds.

Astaxanthin is a carotenoid compound found mostly in animal organisms but also in yeast, plants, algae and microorganisms. This compound and other related carotenoid compounds give the reddish hue to many crustacean species and to their natural predators such as salmon, trout and related species. However, astaxanthin is not naturally present in typical feed sources used in the aquacultural production of such fish species. It is typically added to feed compositions to render the fish its natural color to increase consumer appreciation and market value.

Astaxanthin has also been used as a nutritional supplement for humans, based particularly on its properties as a powerful antioxidant. A growing body of scientific evidence demonstrates that the antioxidant properties of astaxanthin surpasses those of vitamin C, vitamin E, beta-carotene, and other carotenoids.

Synthetic astaxanthin is commercially available but at a high cost. The related carotenoid compound canthaxanthin can be used as a substitute but does not provide as high quality products. Various methods for isolating astaxanthin from natural sources have been suggested such as by extraction with edible oils at high temperatures (U.S. Pat. No. 3,906,112; U.S. Pat. No. 4,505,936), using organic solvents such as carboxylic acid alkyl esters (EP 077,583), chloroform (JP 118,226), or solvent mixtures (JP 11,049,972); boiling lye (U.S. Pat. No. 5,210,186), and hydrochloric acid (JP 9,301,950), and also by enzymatic methods (e.g. CA 1,313,835) where carotenoproteins are extracted with proteases from uncooked shrimp Waste (shells, heads, claws, etc. from shrimp pilling)

The present invention provides a method for isolating astaxanthin and other organic, primarily hydrophobic compounds including other carotenoids from liquid media by adsorption on to a natural substrate comprising fish scales. The method is useful for isolating and concentrating natural compounds such as natural pigments from a solution and the inventors have found that astaxanthin that is present in the run-off water from crustacean processing can be adsorbed by the method and utilized. The method can similarly be used to recover astaxanthin that has been separated from shellfish waste.

The fish scales with the adsorbed compound act in-the way to-stabilize the-adsorbed compound, e.g. pigments like astaxanthin which are susceptible to deterioration due to oxidation, heating and exposure to light.

The fish scales with the adsorbed compound can be used as a direct source of the compound, and or the compound can be separated from the scales with appropriate means.

SUMMARY OF THE INVENTION

In a first aspect, the invention provides a method for recovery of a compound from a liquid medium, comprising the steps of: contacting a medium comprising the compound with fish scales to allow adsorption of the compound to the fish scales; separating the fish scales with the adsorbed compound from the medium to obtain the recovered compound adsorbed onto the fish scales; and optionally desorbing the compound with a suitable solvent.

In a further aspect, fish scales with an adsorbed compound are provided for use as a source of the compound.

In yet a further aspect, the invention provides a method of affecting the color of an animal or an animal product with a pigment comprising providing the animal with ground fish scales with adsorbed pigment.

In a further aspect, compounds obtained by the method of the invention are provided.

In a still further aspect if the invention, methods for purifying wastewater are provided, comprising filtering wastewater through a filter comprising whole or ground fish scales.

The invention provides in an additional aspect feed compositions comprising fish scales with adsorbed pigment.

As a further aspect, the invention provides the use of fish scales with an adsorbed compound as a nutritional supplement or nutraceutical for humans.

DETAILED DESCRIPTION OF THE INVENTION

The method according to the invention for recovery of compounds by adsorption to fish scales is applicable to all compounds with the appropriate adsorptive characteristics such that they adsorb to fish scales. These compounds comprise in particular hydrophobic compounds, including compounds comprising both linear and cyclic polyene structures, both carbocyclic and heterocyclic structures. As the accompanying examples demonstrate, several selected candidate compounds were tested and it was observed that the sorption effect of the fish scales is relatively unspecific, and that the sorption is particularly effective for compounds comprising hydrophobic linear or cyclic polyene structures, such as isoprenoid compounds. Such polyene compounds with conjugated doublebonds with or without heteroatoms include as mentioned above many natural and synthetic pigments which the methods of the invention may beneficially be applied to. In certain preferred embodiments the compounds comprise terpenoids, particularly carotenoid compounds including both carotenes and xanthophylls; and linear tetrapyrroles. In particular embodiments the compound which is adsorbed is astaxanthin, vulgastaxanthin, zeaxanthin, canthaxanthin, violaxanthin, neoxanthin, lutein, lycopene, crocetin, bixin, norbixin, betanin, β-carotene, α-carotene, γ-carotene, δ-carotene, retinol, astacin, betanin, vulgaxanthins, bixin, norbixin, crocetin and also porphyrin compounds such as chlorophylls, phycobilin pigments such as phycoerythrin and phycocyanin; marennine, which is found in nature in the diatom *Haslea ostrearia*; carotenes including β-carotene, α-carotene, γ-carotene, and δ-carotene; retinol; tocopherols; phytols; squalene; and polyunsaturated fatty acids including eicosapentaenoic acid, docosahexaenoic acid and arachidonic acid.

As mentioned, the method comprises the step of contacting a medium comprising the compound with fish scales to allow adsorption of the compound to the fish scales. In this context a medium refers to a solution, emulsion or a suspension. In useful embodiments the medium comprises an aqueous solution or a dominantly or partially aqueous medium such as an aqueous or semi-aqueous emulsion or suspension, which may comprise, e.g. and dissolved, suspended or emulsified organic material including proteins, carbohydrates, and lipids. The medium may further comprise an organic solvent in a fraction in the range of about 0–100%, provided that the solvent fraction does not render the adsorption to ineffective to be useful.

For contacting the medium with the fish scales, the scales may be placed in suitable filtering means, through which the liquid medium is filtered, which means will depend on the particular medium and scale of operation. Optionally, the scales may be placed directly in the liquid medium, and subsequently separated from the medium, e.g. by mechanical filtration such as a conventional filter press. Suitable filtering means are well known in the art and include flow-through pipes where the filtering material is held in place between meshes. The scales may then be cleaned with suitable means if needed prior to further use.

In a particular embodiment of the invention, the compound astaxanthin is recovered from the run-off water from fish or crustacean processing. In such embodiments the crustacean species is any species containing astaxanthin such as shrimp, lobster, crab, crayfish, and krill. In these species, astaxanthin is protein-bound in the live animals but is released upon pre-cooking, such as is done before pilling of shrimps and for other crustacean processing. After such processing, much astaxanthin is still contained in the shell and other waste material, but a significant portion is suspended in the run-off water from the processing, which typically shows a reddish hue polluting the wastewater stream. Consequently, removing or reducing the color of crustacean wastewater is a useful feature of the invention. It is contemplated that such purification may simplify recycling of wastewater and reduce water use in such processing which e.g. for shrimp processing, typically is on the order of 40–80 tons per ton of product.

The invention may also be used to recover pigment which is removed from the solid waste material to a liquid medium such as by enzymatic means.

Any fish scales may be used according to the invention, provided that they have such surface adsorptive characteristics that will provide sufficient adsorption efficiency. Preferably the fish scales are from a bony fish (Osteichthyes) species having cycloid or ctenoid type fish scales. We have found that in particular the latter provide good adsorption properties. (For a detailed discussion on different types and structure of fish scales see, e.g., Lagler et al. Ichthyology, John Wiley & Sons, New York, 1962.)

In useful embodiments of the invention, the scales are from a species of a family selected from the group containing the Gadidae, Scorpaenidae, Clupeidae, and Argentinidae families.

In preferred embodiments the fish scales are from a fish species selected from a group containing redfish (Ocean Perch), Blue-Mouth, Rosefish, Orange Roughy, Rockfish, Capelin, Herring, Sardine, Silver smelt, Snapper, Sea bass, Turbot, Plaice, and other fish species with similar surface-characteristic fish scales.

Highly useful embodiments employ Redfish scales, which are ctenoidal type with distinctive scierit formations. The sclerits are concentric, toothlike striations on the caudal part (the part protruding from the skin) of the scales. Fish scales with such surface-characteristics are currently preferred according to the invention.

In certain embodiments of the invention the provided methods include a step of desorbing the compound from the fish scales with a suitable solvent. Useful solvents are e.g. alkanes including hexane, heptane, octane, and petroleum ether; aromatic hydrocarbons, chlorinated hydrocarbons such as chloroform, phenols, acetonitrile, diethylether, ketones such as acetone, ethers, and mixtures thereof.

The compound(s) may optionally be extracted from fish scales by the use of carbondioxide under super-critical conditions. The carbondioxide may optionally be used in combination with suitable entrainers such as organic solvents, especially solvents of the above-mentioned types.

In a particular, useful embodiment of the invention, the compound is desorbed from the fish scales with a food- or feed-grade oil of animal or vegetable origin. Such methods thus provide an oil product comprising a desired compound, e.g. a pigment such as astaxanthin which may used for human or animal consumption, either directly or as an ingredient in other feed or food products, e.g. baked goods or dairy products where the addition of a compound such as a natural pigment or antioxidant is desired.

It is contemplated that fish scales for use in the methods of the invention may be chemically modified, e.g. by covalent attachment of chemical groups to the surface of the fish scales, to modify their properties such as to obtain more effective and/or more specific adsorption of desired compounds, and such fish scales and their use fall within the general concept of the current invention. Methods to immobilize desired compounds (e.g., synthetic polymers, peptides, carbohydrates, or other organic molecules) are well known in the art.

The novel and useful features of fish scales may further aid in the development and synthesis of new adsorbent materials, based on the chemical and structural properties of fish scales. It is thus an additional aspect of the invention that based on the findings described herein, compounds that adsorb to fish scales may be adsorbed to synthetic fish scale-like material. Such materials would preferably have the essential features of fish scales believed to render the scales their adsorptive properties, i.e. macroscopic (scierit-like) and microscopic (collagen/apatite-like) properties.

In a further aspect, the invention provides fish scales as described above with an adsorbed compound for use as a source of the compound. Such a compound may be any of the above-mentioned, having the chemical features described above, such that they adsorb to fish scales. Preferred embodiments include fish scales with adsorbed natural or synthetic pigments, such as any of the above-mentioned type. In a highly preferred embodiment fish scales with adsorbed astaxanthin are provided as a source of astaxanthin.

It will be greatly appreciated that such fish scale material with one or more adsorbed compounds of nutritional value can be provided for human consumption as a nutritional supplement or a nutraceutical. The chemical composition of fish scales is similar to that of bones, comprising about 30% protein and providing a rich source of calcium in the form of apatite. Fish scale material derived from sardine scales has been sold for human consumption. Fish scale material acts both as a useful calcium source, beneficial to prevent or reduce osteoporosis, and the protein portion of scales which is mostly collagen and elastin is also of nutritional value. The current invention provides all the benefits of fish scale material, with the additional health benefits deriving from the adsorbed material. Useful embodiments of such materials for human consumption include scales with adsorbed vitamins, antioxidants, polyunsatured fatty acids, and any of the above-mentioned compounds that are beneficial for human consumption. Preferred embodiments contain adsorbed retinol (vitamin A), tocopherols, carotene, astaxanthin, squalene, and poyunsaturated fatty acids including eicosapentaenoic acid, docosahexaenoic acid, arachidonic acid, or combinations thereof. As discussed above, the antioxidant properties of astaxanthin make astaxanthin-fish scales a particularly useful supplement. Such fish scales products may additionally be mixed with further beneficial components such as vitamins, flavoring agents, or coloring agents.

Another aspect of the invention provides compounds obtained by the methods of the invention, such as any of the above-mentioned compounds which may not be readily obtained on a commercially economical scale otherwise.

In a further aspect, the invention provides a method of affecting the color of an animal or an animal product with a pigment such as astaxanthin comprising providing the animal with ground fish scales with the adsorbed pigment. It is known that a reddish pigmentation of the meat of animals and/or of products produced by animals may be obtained by administering feed containing astaxanthin to the animals. Useful embodiments include affecting the color of meat from aquacultured species such as salmon and trout; poultry meat, egg yolk, and milk such as to affect the color of butter.

For such purposes the invention provides in yet a further aspect feed compositions comprising fish scales with adsorbed pigment. Such feed compositions are useful for feeding marine species including salmon and trout; poultry species including hens, turkeys, geese; and cattle. The fish scales may be ground to an appropriate grain size depending the texture of the bulk of the feed and the species which is to be fed. The amount of the feed containing the fish scales and/or the amount of fish scales in the feed will depend upon the animal species in question and upon the effect which is desired to be obtained by means of the pigment. In preferred embodiments the pigment is astaxanthin.

In a further aspect of the invention methods are provided for purifying wastewater comprising filtering wastewater with filtering means comprising whole or ground fish scales. As described earlier, such methods are particularly useful in processing plants for crustacean products that contain astaxanthin. The methods of the invention also find use in other industries where compounds such as the above-mentioned are released into wastewater. Useful embodiments include purifying waste streams from textile factories and food plants where pigments are used such as those above-mentioned, or related compounds with the chemical characteristics such that they adsorb to fish scales.

According to the invention, the purification method of the invention comprises essentially removing or reducing the wastewater content of one or more compounds that adsorb to fish scales. The fish scale adsorption process may be a step in a more comprehensive purification process.

EXAMPLES

Example 1

Preparation of Fish Scales

Fish skin from Ocean Perch (*Sebastes marinus*) was de-scaled and the scales collected and washed repeatedly in warm tap water. The scales were dried overnight at 60° C. and stored at room temperature in plastic bags. They were used intact or ground to about 1 mm or 2 mm grain size.

Example 2

Sorption of Fish Scales

Fish scales prepared as in Example 1, whole or ground, were placed in columns with diameters 2.5 to 5 cm with lengths no longer than 10 cm. The flow was by gravity force alone.

2a) Sorption of Astaxanthin from Shrimp Processing Run-Off Water 1L of shrimp processing wastewater was passed through a scales filter column with 4 g ground scales prepared as in Example 1. The flow was about 3 mumin. The experiment was run in reduced light conditions and at room temperature. 5 samples were then analysed with HPLC (described below). The samples were the following:

1. wastewater (with floating suspension)
2. the first 25 mm of suspension settled on the top of the scales column
3. the following 10 mm of scales with sorbed pigment
4. next 10 mm of the same material
5. the bottom 25 mm of the scales column It could be observed that the pink color spread quite uniformly within the column packed with scale material, although gradually loosing its intensity towards the bottom. This shows that retention of the pigment onto scales is not only due to the mechanical filtration of wastewater suspension at the top of the scales column but also occur in the deeper layers of the scales.

TABLE 1

Astaxanthin in samples 2–5 (mg/kg dry wt.) and sample 1 (mg/L)

| sample | free Astaxanhine | esterified Astaxanthine | total |
|---|---|---|---|
| 1 | 0.15 | 0.49 | 0.65 |
| 2 | 11.9 | 93.2 | 105.1 |
| 3 | 18.4 | 343.0 | 362.1 |
| 4 | 10.0 | 114.8 | 124.8 |
| 5 | 4.32 | 38.4 | 42.7 |

For HPLC analysis, the samples were extracted with a 1:1 mixture of petroleum ether (bp. 40°–60°):acetone, sonicated and centrifuged. Subsamples were saponified with KOH (procedure of Britton G. et al. *Carotenois—Isolation and Analysis*, Birkhäuser, Basel, 1995). Controls were run with synthetic, pure astaxanthin.

The results demonstrate that retention of the pigment onto scales is not only due to the mechanical filtration of wastewater suspension at the top of the scales column but also occur in the deeper layers of the scales. The quantitative analysis shows that over 97% of the pigment remains on the scales.

2b) Sorption of Synthetic Pure Synthetic Astaxanthin

Pure astaxanthin (Sigma Chemicals) was obtained and dissolved in a water-acetone mixture. With an acetone concentration of about 0.5% and 10 mM NaCl, the sorption of astaxanthin occurs with comparable efficiency compared to wastewater pigment.

2c) Comparing Sorption of Different Compounds

A few selected candidate compounds were tested and their sorption to fish scales compared to that of astaxanthin. The compounds are carotene, spinach extract containing chlorophyll a and b, neoxanthin, lutein, and violaxanthin. The solutions were adjusted to a 10 mM NaCl concentration and about 0.5% acetone. The results of sorption efficiency are presented in FIG. 1.

The highest sorption efficiency was observed for β-carotene. Other carotenoids (including astaxanthin) and both chlorophylls are bound with comparable efficiency in the range of 60–67% pigment remaining on the fish scales. The β-carotene is more unpolar in comparison to the other carotenoids which are hydroxy-carotenoids (xanthophylls), indicating that the sorption effect may depend primarily on the hydrophobic polyene structure these compounds have in common. The results show that the sorption effect of the fish scales is rather unspecific with respect to the classes of compounds tested.

2d) Effect of Scale Size, Ground vs. Whole Scales

Columns were prepared as earlier with whole scales and medium-ground scales and tested with shrimp processing run-off water. The ground scales showed higher binding efficiency (% retained astaxanthin) and load capacity (mL sample liquid/g) than whole fish scales, which however also retained pigment.

Example 3

Desorption of Astaxanthin From Fish Scales

Figure 2:
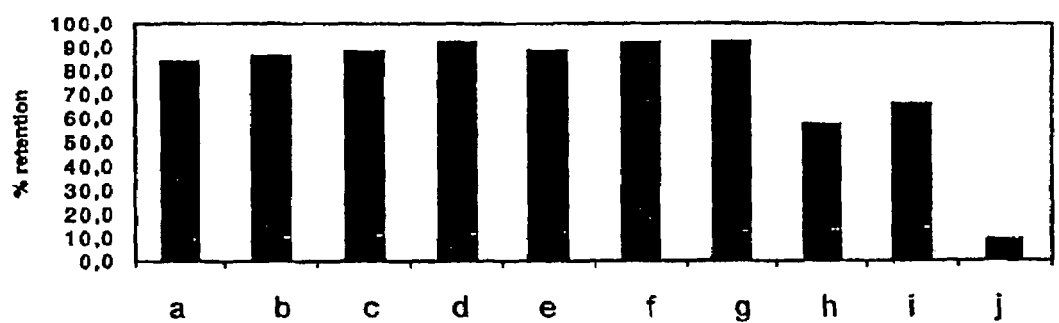

Desorption of astaxanthin from scales was studied using different solvents as eluents. Water, methanol (10, 20, 50, and 100%), acetonitrile, 2-propanol, hexane and petroleum ether (40°–60°) were compared. The results are represented in FIG. 2. No desorption is observed with water and nor the alcohols tested. Comparable elution efficiency is observed with acetonitrile and hexane, but highest efficiency was obtained with petroleum ether.

LEGENDS TO FIGURES

FIG. 1: Sorption efficiency of different compounds adsorbed to fish scales as discussed in Example 2c). The compounds were measured spectrophotometrically as % of pigment remaining on fish scales compared to total amount dissolved in sample filtered through the fish scales. a: astaxanthin, b: β carotene, c: chlorophyll a, d: chlorophyll b, e: lutein, f: violaxanthin, g: neoxanthin.

FIG. 2: Retention of astaxanthin on fish scales after desorption with different solvents, as explained in Example 3. a: Shrimp wastewater, b: water, c–f: 10%–20%–50%–100% methanol in water, g: acetonitrile, h: 2-propanol, i: hexane, j: petroleum ether (40°–60°). Y-scale shows % retained pigment measured spectrophotometrically.

Figure 3:
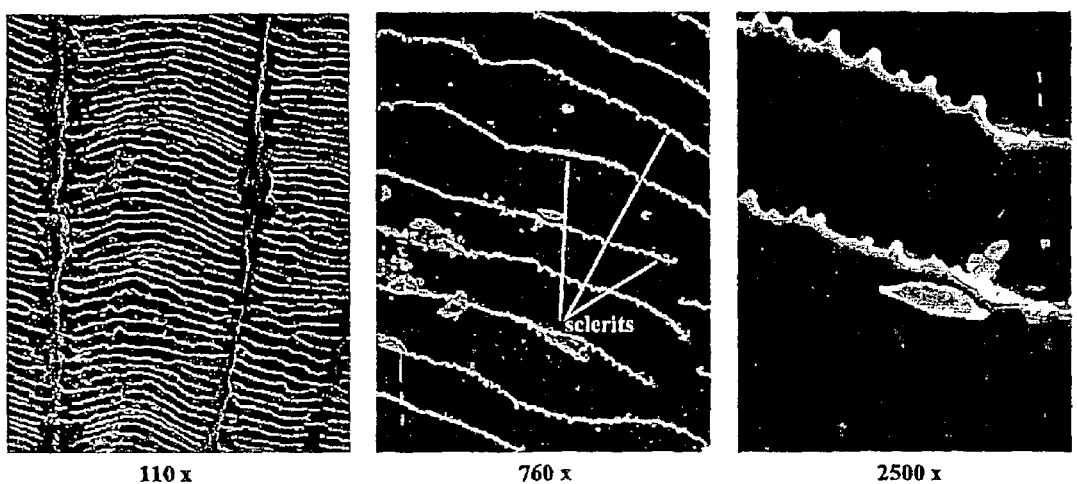
Figure 3:
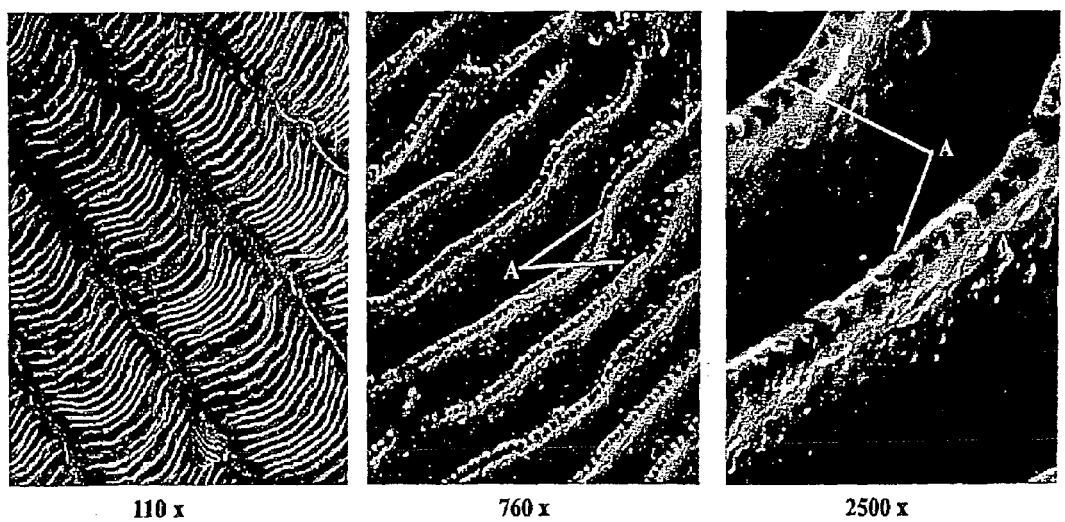

FIG. 3: Electron microscopy images of fish scales from Ocean Perch, showing tooth structure (sclerits) of the scales which astaxanthin seems to adsorb to preferentially. The upper panel shows a clean fish scale at different magnification, where arrows on the center panel point to sclerits. The lower panel show a scale after contact with astaxanthin-containing shrimp wastewater (as described in Example 2a) and it is clearly observed that material is retained, in particular on the sclerits.

The invention claimed is:

1. A method for recovery of a hydrophobic compound from a liquid medium, comprising the steps of:
    (i) contacting a medium comprising the compound with fish scales to allow adsorption of the compound to the fish scales;
    (ii) separating the fish scales with the adsorbed compound from the medium to obtain the recovered compound adsorbed onto the fish scales; and
    (iii) optionally desorbing the compound with a suitable solvent.

2. The method according to claim 1, wherein the compound is a substantially hydrophobic compound, comprising a linear or cyclic polyene-structure with conjugated double bonds with or without heteroatoms.

3. The method according to claim 1, wherein the compound is selected from the group containing carotenoids, porphyrins, and linear tetrapyrroles.

4. The method according to claim 1, wherein the compound is selected from the group containing chlorophylls, chlorophyllides, protoporphyrin, ferroprotoporphyrin; phycobilin, biliverdin, bilirudin; marennine; carotenoids, both xanthophylls including astaxanthin, vulgastaxanthin, zeaxanthin, canthaxanthin, vioaxanthin, lutein, lycopene, crocetin, bixin, norbixin, betanin; and carotenes including β-carotene, α-carotene, γ-carotene, and δ-carotene; retinol; tocopherols; phytols; squalene; polyunsaturated fatty acids including eicosapentaenoic acid, docosahexaenoic acid, and arachidonic acid.

5. The method according to claim 1, wherein the compound is a carotenoid compound.

6. The method according to claim 5, wherein the compound is astaxanthin.

7. The method according to claim 6, wherein astaxanthin is recovered from the run-off water from fish or crustacean processing.

8. The method according to claim 7, wherein the crustacean is a species selected from the group containing shrimp, lobster, crab, crayfish, and krill.

9. The method according to claim 1, wherein the fish scales are from a bony fish (Osteichthyes) species having cycloid or ctenoid structural-type fish scales.

10. The method according to claim 9, wherein the scales are from a species of a family selected from the group containing the Gadidae, Scorpaenidae, Clupeidae, Argentinidae families.

11. The method according to claim 1, wherein the fish scales are from a fish species selected from a group containing Ocean Perch (Redfish), Blue-Mouth, Rosefish, Orange Roughy, Rockflsh, Capelin, Herring, Sardine, Silver smelt, Snapper, Sea bass, Turbot and Plaice.

12. The method according to claim 1, wherein the fish scales are ground scales.

13. The method according to claim 1, wherein the fish scales are chemically modified.

14. The method according to claim 1, where the compound is desorbed from the fish scales with a food- or feed-grade oil of animal or vegetable origin.

15. Isolated fish scales comprising an adsorbed hydrophobic compound.

16. The fish scales according to claim 15, wherein the hydrophobic compound comprises a natural pigment.

17. The fish scales according to claim 15, wherein the adsorbed hydrophobic compound comprises chlorophylls, chlorophyllides, protoporphyrin, ferroprotoporphyrin; linear tetrapyrroles; carotenoids; astaxanthin, vulgastaxanthin, zeaxanthin, canthaxanthin, vioaxanthin, lutein, lycopene, crocetin, bixin, norbixin, betanin; and carotenes;

retinol, tocopherols, phytols, steroids or polyunsaturated fatty acids.

18. The fish scales according to claim 15, comprising astaxanthin.

19. The fish scales according to claim 15, wherein the scales are from a species of a family comprising the Gadidae, Scorpaenidae, Clupeidae, and Argentinidae families.

20. The fish scales according to claim 15, wherein the scales are from a fish comprising Ocean Perch (Redfish), Blue-Mouth, Rosefish, Orange Roughy, Rockfish, Capelin, Herring, Sardine, Silver smelt, Snapper, Sea bass, Turbot and or Plaice.

21. The fish scales according to claim 15 that are chemically modified.

22. Isolated fish scales comprising an adsorbed hydrophobic compound and which compound is adsorptive on fish scales for use as a nutritional and/or nutraceutical supplement for humans.

23. The fish scales according to claim 17, wherein the linear tetrapyrroles comprise phycobilin, biliverdin, bilirubin or marennine; the carotenoids include carotenes or xanthophylls; the steroids include squalene; the polyunsaturated fatty acids include eicosapentaenoic acid, docosahexanoic acid or arachidonic acid; and the carotenes include $\beta$-carotene, $\alpha$-carotene, $\gamma$-carotene, or $\delta$-carotene.

24. The fish scales according to claim 22, where the adsorbed hydrophobic compound comprises astaxanthin, vulgastaxanthin, zeaxanthin, canthaxanthin, violaxanthin, carotene, retinol, tocopherol, squalene;

protoporphyrin, ferroprotoporfyrin, polyunsaturated fatty acids including eicosapentaenoic acid, docosahexaenoic acid, and arachidonic acid.

25. The fish scales according to claim 22 where the adsorbed hydrophobic compound is a carotenoid.

26. The fish scales according to claim 22 where the adsorbed hydrophobic compound is astaxanthin.

27. A method of affecting the color of an animal or an animal product with a pigment comprising providing the animal with ground fish scales with adsorbed pigment.

28. A feed composition comprising fish scales with adsorbed pigment.

29. The feed composition according to claim 28, for feeding fish species including salmon and trout; poultry including hens, turkeys, geese; and cattle.

30. The feed composition according to claim 28, wherein the pigment is astaxanthin.

31. The method according to claim 1, where the compound is desorbed from the fish scales with a solvent comprising alkanes, aromatic hydrocarbons, chlorinated hydrocarbons, phenols, acetonitrile, diethylether, ketones, ethers or mixtures thereof.

32. The method according to claim 31, where the alkanes include hexane, heptane, octane, petroleum ether or mixtures thereof.

33. The method according to claim 31, where ketones include acetone.

* * * * *